(12) United States Patent
Togami

(10) Patent No.: US 9,600,149 B2
(45) Date of Patent: Mar. 21, 2017

(54) DISPLAY PROCESSING SYSTEM, DISPLAY PROCESSING METHOD, AND INFORMATION STORAGE MEDIUM

(75) Inventor: Junko Togami, Tokyo (JP)

(73) Assignee: NEC CORPORATION, Tokyo (JP)

( * ) Notice: Subject to any disclaimer, the term of this patent is extended or adjusted under 35 U.S.C. 154(b) by 881 days.

(21) Appl. No.: 13/807,216

(22) PCT Filed: May 25, 2011

(86) PCT No.: PCT/JP2011/002923
§ 371 (c)(1),
(2), (4) Date: Dec. 27, 2012

(87) PCT Pub. No.: WO2012/008082
PCT Pub. Date: Jan. 19, 2012

(65) Prior Publication Data
US 2013/0111388 A1  May 2, 2013

(30) Foreign Application Priority Data
Jul. 15, 2010  (JP) ................................ 2010-160351

(51) Int. Cl.
G06F 3/048  (2013.01)
G06F 3/0484 (2013.01)
G06F 19/00  (2011.01)

(52) U.S. Cl.
CPC ........ *G06F 3/0484* (2013.01); *G06F 19/3437* (2013.01)

(58) Field of Classification Search
None
See application file for complete search history.

(56) References Cited

U.S. PATENT DOCUMENTS 5,918,217 A * 6/1999 Maggioncalda ... G06Q 30/0601
   705/36 R
8,370,243 B1 * 2/2013 Cernyar ..................... 705/36 R

FOREIGN PATENT DOCUMENTS

JP  11-085857 A   3/1999
JP  2002-183241 A  6/2002
(Continued)

OTHER PUBLICATIONS

Communication dated Apr. 7, 2015 from the Japanese Patent Office in counterpart application No. 2012-524404.
(Continued)

*Primary Examiner* — William Trapanese
(74) *Attorney, Agent, or Firm* — Sughrue Mion, PLLC

(57) ABSTRACT

It is possible for a user to intuitively and efficiently set a predetermined condition for each parameter. A display processing system includes GUI display means for displaying a plurality of parameter components (103) corresponding to a plurality of parameters and a plurality of parameter condition components (104) corresponding to a plurality of conditions set to a plurality of parameters (103) on a display, and condition specification means for associating one parameter condition component (104) with a first parameter component (103) by means of the display position of the first parameter component (103) and the display position of each of a plurality of parameter condition components (104), and specifying the condition corresponding to the parameter condition component (104) as a condition set to the parameter corresponding to the first parameter component (103).

7 Claims, 20 Drawing Sheets

(56) References Cited

FOREIGN PATENT DOCUMENTS

| | | |
|---|---|---|
| JP | 2005-267025 A | 9/2005 |
| JP | 2006-340039 A | 12/2006 |
| JP | 2009-295047 A | 12/2009 |
| JP | 2010-41616 A | 2/2010 |
| WO | 2007/066663 A1 | 6/2007 |

OTHER PUBLICATIONS

Togami et al., "Proposal for a New Simulation User Interface," 2010, pp. 135-138 (4 pages total).

* cited by examiner

FIG. 16

| PARAMETER CONDITION ||
|---|---|
| DEGREE-OF-VARIATION ACQUISITION INFORMATION | COMPUTER CONDITION |
| FULL OF MOTIVATION | VALUE (X) OF PARAMETER MAY CHANGE FROM PREDETERMINED VALUE (Y) IN DIRECTION OF EXTENSION OF LIFE SPAN IF POSSIBLE (Y $\leq$ X OR X $\leq$ Y) |
| MOTIVATED | VALUE (X) OF PARAMETER MAY CHANGE FROM PREDETERMINED VALUE (Y) AT CHANGE RATE OF 25% IN DIRECTION OF EXTENSION OF LIFE SPAN (Y $\leq$ X $\leq$ 1.25Y OR 0.75Y $\leq$ X $\leq$ Y) |
| UNMOTIVATED | VALUE (X) OF PARAMETER MAY NOT CHANGE FROM PREDETERMINED VALUE (Y) (X=Y) |
| DECIDE | VALUE (X) OF PARAMETER MAY NOT CHANGE FROM SUGGESTED PARAMETER VALUE (Z) WHEN "DECIDE" IS SET (X = Z) |

| PARAMETER CONDITION | |
|---|---|
| DEGREE-OF-VARIATION ACQUISITION INFORMATION | COMPUTER CONDITION |
| NOT WANT TO CHANGE | FIX TO VALUE INPUT BY USER |
| PERSEVERE | MAXIMIZE IN DIRECTION OF EXTENSION OF LIFE SPAN |
| EXECUTE | FIX TO RECOMMENDED VALUE OF SYSTEM WHEN CONSTRAINT CONDITION IS DESIGNATED TO "EXECUTE" |

| PARAMETER CONDITION | |
|---|---|
| DEGREE-OF-VARIATION ACQUISITION INFORMATION | COMPUTER CONDITION |
| NOT WANT TO CHANGE | FIX TO VALUE INPUT BY USER |
| PERSEVERE | SET CHANGE RATE TO 25% OF PRESENT VALUE |
| PERSEVERE AS MUCH AS POSSIBLE | SET CHANGE RATE TO 50% OF PRESENT VALUE |
| EXECUTE | FIX TO RECOMMENDED VALUE OF SYSTEM WHEN CONSTRAINT CONDITION IS DESIGNATED TO "EXECUTE" |

| PARAMETER CONDITION | |
|---|---|
| DEGREE-OF-VARIATION ACQUISITION INFORMATION | COMPUTER CONDITION |
| NOT SELL WELL | SET TO VALUE EQUAL TO OR GREATER 1 AND EQUAL TO OR SMALLER THAN 5 |
| SELL | SET TO VALUE GREATER THAN VALUE OF PARAMETER UNDER CONSTRAINT CONDITION OF "NOT SELL WELL" |
| SELL WELL | SET TO VALUE GREATER THAN VALUE OF PARAMETER UNDER CONSTRAINT CONDITION OF "SELL" |
| ORDER | SET TO RECOMMENDED VALUE OF SYSTEM WHEN CONSTRAINT CONDITION IS DESIGNATED TO "ORDER" |

40

DISPLAY PROCESSING SYSTEM, DISPLAY PROCESSING METHOD, AND INFORMATION STORAGE MEDIUM

CROSS REFERENCE TO RELATED APPLICATIONS

This application is a National Stage of International Application No. PCT/JP2011/002923 filed May 25, 2011, claiming priority based on Japanese Patent Application No. 2010-160351, filed Jul. 15, 2010, the contents of all of which are incorporated herein by reference in their entirety.

TECHNICAL FIELD

The present invention relates to a display processing system, a display processing method, and a program.

BACKGROUND ART

There is a simulation which calculates a predetermined result (simulation value) from the values of a plurality of parameters. Meanwhile, there is a simulation which calculates a combination of a plurality of parameter values for obtaining a desired result (simulation value). In a system of such a simulation, it is necessary for a user to operate a device and to perform a predetermined input.

Patent Document 1 (Japanese Laid-Open Patent Application No. 2002-183241) describes a system which receives an input of a simulation value and an allowable range as the values of a plurality of parameters from a user, and performs calculation processing of parameter values included in the allowable range using a computer.

RELATED DOCUMENT

Patent Document

[Patent Document 1] Japanese Laid-Open Patent Application No. 2002-183241

DISCLOSURE OF THE INVENTION

However, in the related art, there is a problem in that user-friendliness of user interface in the above-described system of the simulation is not good. For example, in the technique described in Patent Document 1, there is a problem in that it is not possible to intuitively and efficiently receive an input of the values of a plurality of parameters from the user.

An object of the invention is to improve user-friendliness of a user interface in the system of the above-described simulation.

The invention provides a display processing system including GUI display unit for displaying a plurality of parameter components corresponding to a plurality of parameters and a plurality of parameter condition components corresponding to a plurality of conditions set to the plurality of parameters on a display, and condition specification unit for assigning one parameter condition component to a first parameter component by means of the display position of the first parameter component and the display position of each of the plurality of parameter condition components, and specifying the condition corresponding to the parameter condition component as the condition set to the parameter corresponding to the first parameter component.

The invention also provides a program which causes a computer to function as GUI display unit for displaying a plurality of parameter components corresponding to a plurality of parameters and a plurality of parameter condition components corresponding to a plurality of conditions set to the plurality of parameters on a display, and condition specification unit for assigning one parameter condition component to a first parameter component by means of the display position of the first parameter component and the display position of each of the plurality of parameter condition components, and specifying the condition corresponding to the parameter condition component as the condition set to the parameter corresponding to the first parameter component.

The invention also provides a display processing method including a GUI display step of displaying a plurality of parameter components corresponding to a plurality of parameters and a plurality of parameter condition components corresponding to a plurality of conditions set to the plurality of parameters on a display, and a condition specification step of assigning one parameter condition component to a first parameter component by means of the display position of the first parameter component and the display position of each of the plurality of parameter condition components, and specifying the condition corresponding to the parameter condition component as the condition set to the parameter corresponding to the first parameter component.

According to the invention, a display processing system, a display processing method, and a program which allows the user to intuitively and efficiently set a predetermined condition to each parameter are realized.

BRIEF DESCRIPTION OF THE DRAWINGS

The above and other objects, features, and advantages will be apparent from the following embodiment and the accompanying drawings.

FIG. 16 is a diagram showing an example of a part of the internal configuration of a condition holding unit of the simulation system of this embodiment.

FIG. 17 is a diagram showing an example of a part of the internal configuration of a condition holding unit of the simulation system of this embodiment.

FIG. 18 is a diagram showing an example of a part of the internal configuration of a condition holding unit of the simulation system of this embodiment.

FIG. 19 is a diagram showing an example of a part of the internal configuration of a condition holding unit of the simulation system of this embodiment.

DESCRIPTION OF EMBODIMENTS

Figure 1:
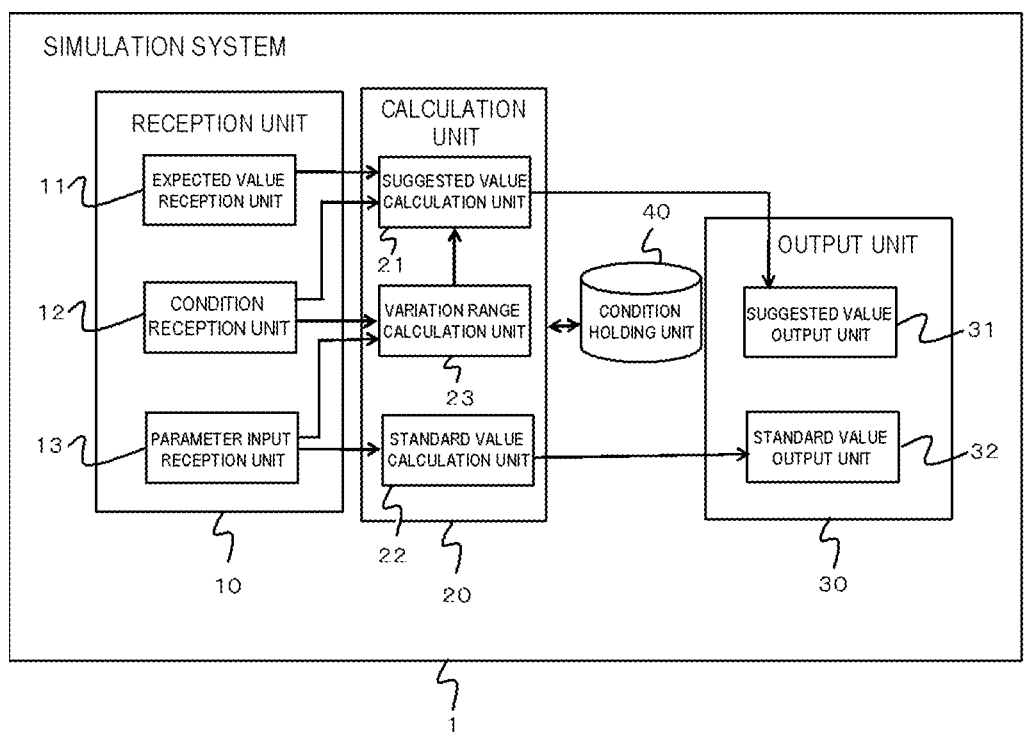
FIG. 1 is an example of a functional block diagram of a simulation system of this embodiment.

Hereinafter, embodiments of the invention will be described with reference to the drawings. In all of the drawings and the description in the specification, the same constituent elements are represented by the same reference numerals, and description will not be repeated appropriately.

The respective units of a display processing system of the invention are realized by an arbitrary combination of hardware and software centering on a CPU and a memory of an arbitrary computer, a program loaded on the memory (including a program stored in the memory in advance when shipping or a program downloaded from a storage medium, such as a CD, or a server or the like on a network), a storage unit, such as a hard disk, which stores the program, and a network connection interface. It should be understood by those skilled in the art that the realization method and the system may be modified in various ways.

A functional block diagram in the following description shows blocks in terms of functions instead of a configuration in terms of hardware. Although in these drawings, a case where the display processing system is realized by a single device will be described, realization unit is not limited thereto. That is, the display processing system may be constituted by a combination of devices physically divided.

In the following embodiment, an example where the display processing system of the invention is a simulation system will be described. A simulation system which will be described in the following embodiment calculates the values of a plurality of parameters such that the result (simulation value) of calculation from a plurality of parameters becomes an expected value through a first simulation.

The first simulation corresponds to every simulation which receives the values of a plurality of parameters as input, and calculates a result through predetermined calculation processing. The first simulation may be, for example, a life span prediction simulation, a disease onset prediction simulation, a housing loan repayment period simulation, or an automobile insurance estimation simulation. The first simulation may be a prediction simulation for efficient sales in a business, such as a store sales prediction simulation, a product sales prediction simulation, or a product ordering simulation. The first simulation may be a simulation for natural or man-made disaster prevention, such as a disaster scale prediction simulation or a total loss prediction simulation at the time of a disaster. The first simulation may be a design simulation for buildings, construction machinery, automobiles, electronic circuits, and antennas, or a radio propagation simulation. The above is for illustration, and the invention is not limited thereto.

<First Embodiment>

In this embodiment, description will be provided as to an example where the first simulation is a life span prediction system which calculates a predictive life span from the values of a plurality of parameters (vegetable intake amount, sleeping time, extra work time, smoking amount, and the like) representing a life style as a simulation value.

FIG. 1 is a functional block diagram showing an example of the configuration of a simulation system 1 of this embodiment.

As shown in the drawing, the simulation system 1 has a reception unit 10, a calculation unit 20, an output unit 30, and a condition holding unit 40.

The reception unit 10 is configured to receive an input from a user. Means for realizing the reception unit 10 is not particularly limited, and the reception unit 10 may be realized by applying, for example, all sorts of input devices, such as a keyboard, a mouse, a touch panel, and input buttons provided in a device. As shown in FIG. 1, the reception unit 10 has an expected value reception unit 11, a condition reception unit 12, and a parameter input reception unit 13.

The calculation unit 20 is configured to perform predetermined calculation processing in accordance with a program. Means for realizing the calculation unit 20 is not particularly limited, and the calculation unit 20 may be realized by applying, for example, a CPU or the like. As shown in FIG. 1, the calculation unit 20 has a suggested value calculation unit 21, a standard value calculation unit 22, and a variation range calculation unit 23.

The output unit 30 is configured to output a calculation result of the calculation unit 20. Means for realizing the output unit 30 is not particularly limited, and the output unit 30 may be realized by applying, for example, all sorts of output devices, such as a display, a speaker, a printing device, a mail transmission device, a facsimile device, and the like. As shown in FIG. 1, the output unit 30 has a suggested value output unit 31 and a standard value output unit 32.

The condition holding unit 40 is a memory which stores electronic data. The condition holding unit 40 will be described below.

Hereinafter, the configuration of each unit will be described in detail.

The parameter input reception unit 13 receives an input of user designated values as the values of a plurality of parameters arbitrarily determined by the user. The user designated values are values which can be arbitrarily determined by the user. For example, the user may input the values of a plurality of parameters (vegetable intake amount, sleeping time, extra work time, smoking amount, and the like) representing the present state of the user as the user designated values. If a value represents the present state of the user, the user can easily understand and input the value. Specific means which is used when the parameter input reception unit 13 receives the user designated value for each parameter is not particularly limited, and may be realized by applying all sorts of input devices.

Figure 2:
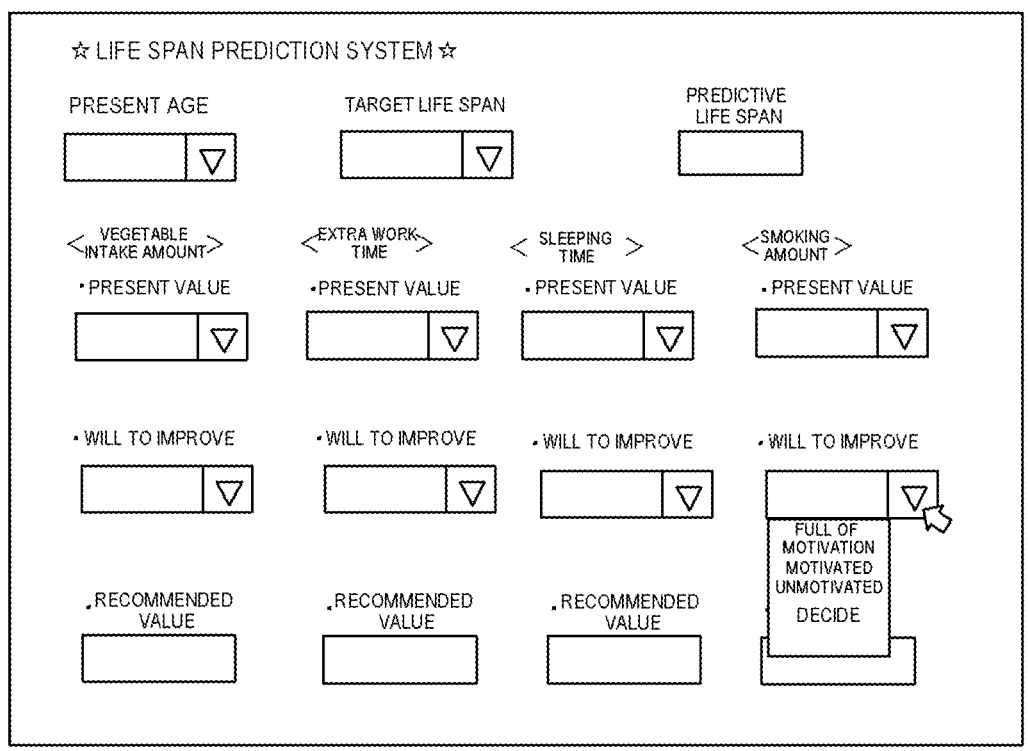
FIG. 2 is a diagram showing an example of a user interface of the simulation system of this embodiment.

FIG. 2 is a diagram showing an example of a display screen which is displayed on the display or the like of the user in the simulation system 1 of this embodiment. In this embodiment, the user may perform a predetermined operation on the display screen to input predetermined information, or the like. For example, the parameter input reception unit 13 may use a user interface shown in FIG. 2 to receive designation of a present value (user designated value) from a pull-down menu in a column "present value" associated with each of a plurality of parameters (vegetable intake amount, extra work time, sleeping time, smoking amount).

The standard value calculation unit 22 calculates a standard value by means of the user designated values received by the parameter input reception unit 13. The standard value is a value (simulation result) which is calculated from the user designated values through a first simulation. In this embodiment, the standard value calculation unit 22 executes the first simulation by means of the user designated values received by the parameter input reception unit 13, and calculates a predictive life span as the standard value.

The timing at which the standard value calculation unit 22 starts to calculate the standard value is not particularly limited, and for example, (1) the timing at which the user designated values (in FIG. 2, the column "present value") are set for all of a plurality of parameters may be used as a trigger, or (2) though not shown in the user interface of FIG. 2, a button for inputting an instruction to start the calculation of the standard value may be provided, and the timing at which the input of the instruction to start the calculation is received through the button may be used as a trigger.

The standard value output unit 32 outputs the standard value calculated by the standard value calculation unit 22. Specific means which is used when the standard value output unit 32 outputs the standard value is not particularly limited, and may be realized by applying all sorts of output devices. For example, the standard value output unit 32 may output the standard value to a column "predictive life span" in the user interface of FIG. 2.

The expected value reception unit 11 receives an input to designate an expected value from the user. The expected value is a value which is expected by the user as the result (simulation value) of the first simulation.

In this embodiment, the expected value reception unit 11 receives the designation of the value of a life span (for example, 100 years old) which is expected by the user as the expected value. The expected value is a value which may be arbitrarily determined by the user. The user may determine and input a desired expected value with reference to the standard value output by the standard value output unit 32.

Specific means which is used when the expected value reception unit 11 receives the expected value is not particularly limited, and may be realized by applying all sorts of input devices. For example, the expected value reception unit 11 may use the user interface shown in FIG. 2 to receive the designation of the expected value from the pull-down menu in a column "target life span". The user interface shown in FIG. 2 is configured to receive the designation of a present age from the pull-down menu in a column "present age" from the user.

Returning to FIG. 1, the condition holding unit 40 holds a plurality of parameter conditions as a condition representing the degree of allowable variation in the value of each of a plurality of parameters. The "degree of allowable variation" is the degree which is allowed as the value of each of a plurality of parameters such that the user obtains the expected value as the simulation value of the first simulation. FIG. 16 is a diagram showing an example of a part of the internal configuration of the condition holding unit 40 in this embodiment.

As shown in FIG. 16, the "parameter condition" representing the degree of allowable variation is information in which "degree-of-variation understanding information" is assigned to a "computer condition".

The "computer condition" is information for specifically specifying the degree of allowable variation with numerical values. This information is used when the computer calculates the value of each of a plurality of parameters.

The "degree-of-variation understanding information" is information which allows the user to intuitively understand a numerical range (degree of allowable variation) specified by an associated computer condition. This information is used when the user sets any parameter condition to each parameter. The degree-of-variation understanding information is preferably a combination of sentences, figures, numerals, photographs, and the like which can be intuitively understood by the user, instead of a specific numerical value (upper limit and lower limit) of the value of each parameter.

In this embodiment in which the first simulation is a life span prediction system, the parameter condition may include the following.

For example, the parameter condition is as follows:

(1) computer condition: "the value (X) of a parameter may change from a predetermined value (Y) in a direction of extension of the life span if possible ($Y \leq X \leq A$ or $B \leq X \leq Y$. A and B are integers set in advance for each parameter (the same applies to the following).)", and degree-of-variation understanding information: "full of motivation";

(2) computer condition: "the value (X) of a parameter may change from a predetermined value (Y) to a change rate of 25% in a direction of extension of the life span ($Y \leq X \leq 1.25Y \leq A$ or $B \leq 0.75Y \leq X \leq Y$)", and the degree-of-variation understanding information: "motivated";

(3) computer condition: "the value (X) of a parameter does not change from a predetermined value (Y) (X=Y)", and the degree-of-variation understanding information: "unmotivated"; and (4) computer condition: "the value (X) of a parameter does not change from a suggested parameter value (Z) (in FIG. 2, a value displayed in a column "recommended value") when "decide" (degree-of-variation understanding information) is set (X=Z)", and the degree-of-variation understanding information: "decide". The predetermined value (Y) may be a user designated value (a value received by the parameter input reception unit 13 for each parameter, and in FIG. 2, "present value")), or the average value of a Japanese person. When the predetermined value (Y) is the average value of a Japanese person or the like, the simulation system of this embodiment is configured to hold the average value of each parameter or the like in advance or to acquire the average value from another device at a predetermined timing. This value is used in calculation processing for calculating a variation range in the variation range calculation unit 23 described below.

The parameter conditions described above are just an example, and the computer condition and the degree-of-variation understanding information may be arbitrarily set. Hereinafter, other examples of the parameter conditions will be described. The number of parameter conditions may be arbitrarily set. However, if the number of parameter conditions is too large, it takes a lot of time for the user to understand all of multiple parameter conditions. The user may find an operation to determine an appropriate parameter condition from multiple parameter conditions complex. The processing of the simulation system 1 becomes complicated. For this reason, the number of parameter conditions may be equal to or smaller than the number of user-friendly parameter conditions taking into consideration operability for the user to some extent. For example, while in the parameter conditions shown in FIG. 16, as the computer condition for the degree-of-variation understanding information "motivated", the change rate "25%" is defined, this value may be set in a distributed and stepwise manner.

If the number of parameter conditions is limited in this way, the number of parameters which are assigned to one condition can increase and can be processed in groups, and it can be expected that the processing efficiency of the simulation system 1 is improved.

The condition reception unit 12 receives an input to set any parameter condition to each of a plurality of parameters. In this embodiment, the condition reception unit 12 receives the designation of the degree-of-variation understanding information to each parameter from the user as the parameter condition. In this case, the user can understand the degree of allowable variation range of each parameter condition on the basis of the degree-of-variation understanding information, and can determine which parameter condition is set to each parameter. In this way, the user can easily set a condition to each parameter even when the user is not sufficiently familiar with each parameter. Specific means which is used when the condition reception unit 12 receives the setting of the parameter condition to each parameter is not particularly limited, and may be realized by applying all sorts of input devices.

In the user interface shown in FIG. 2, the condition reception unit 12 is configured to receive the designation of the degree-of-variation understanding information (parameter condition) from the pull-down menu in a column "will to improve" associated with each of a plurality of parameters (vegetable intake amount, extra work time, sleeping time, smoking amount) from the user.

In all of the parameters, one parameter condition may be set in advance as an initial setting, and in this state, the condition reception unit 12 may receive an input to change a parameter condition set to a predetermined parameter to a desired parameter condition. The parameter conditions of all of the parameters may be in a blank state in advance, and in this state, the condition reception unit 12 may receive an input to set desired parameter conditions to all of the parameters.

The variation range calculation unit 23 calculates the variation range of each of a plurality of parameters on the basis of the parameter condition designated to each parameter. The variation range specifically specifies an allowable range to each parameter with numerical values. The variation range calculation unit 23 calculates the variation range of the value of each parameter by means of the computer condition included in the parameter condition.

For example, when the computer condition of any parameter condition is that "the value (X) of the parameter may change from the predetermined value (Y) to the change rate of 25% in a direction of extension of the life span ($Y \leq X \leq 1.25Y \leq A$ or $B \leq 0.75Y \leq X \leq Y$)", the variation range calculation unit 23 (1) acquires the user designated value set to each parameter as the predetermined value (Y), (2) understands the direction of extension of the life span for each parameter by means of, for example, information held in advance (for example: in a case of the parameter "smoking amount", the direction in which the value of the parameter is lowered is the direction of extension of the life span), and (3) calculates $Y \leq X \leq 1.25Y$ or $0.75Y \leq X \leq Y$ as the variation range (for example: in the case of the parameter "smoking amount", "$0.75Y \leq X \leq Y$" is calculated).

The variation range calculation unit 23 may acquire a predetermined integer value, such as the average value of a Japanese person of each parameter as the predetermined value (Y) from the simulation system or an external device instead of the user designated value, and may perform the same processing as described above.

With the variation range calculation unit 23, the variation range of each parameter based on the predetermined value (for example: the average value of a Japanese person, the present value of the user, or the like) can be calculated, thereby deciding an appropriate value as the variation range of each parameter.

The suggested value calculation unit 21 calculates a suggested parameter value as the value of each of a plurality of parameters such that the result of the first simulation becomes an expected value on the basis of the set parameter condition. The term "on the basis of the parameter condition" means "under the parameter condition". In this embodiment, this means that the parameter condition (computer condition) set to each parameter is satisfied, specifically, the variation range calculated by the variation range calculation unit 32 for each parameter is filled.

Means which is used when the suggested value calculation unit 21 calculates the suggested parameter value is not particularly limited, and the first simulation may be repeatedly performed while changing one or more values of a plurality of parameters within the variation range until the simulation value becomes the expected value, thereby calculating a desired combination of the values of a plurality of parameters.

The timing at which the suggested value calculation unit 21 starts to calculate the suggested parameter value is not particularly limited, for example, (1) the timing at which the expected value (in FIG. 2, a column "target life span") is designated and any parameter condition (in FIG. 2, the column "will to improve") is set for all of a plurality of parameters may be used as a trigger, or (2) though not shown in the user interface of FIG. 2, a button for inputting an instruction to start the calculation of the suggested parameter value may be provided, and the timing at which the input of the instruction to start the calculation is received through the button may be used as a trigger.

Besides, when the condition reception unit 12 receives change in the parameter condition of one or more parameters in a state where (3) the expected value (in FIG. 2, "target life span") is designated and any parameter condition is set for all of a plurality of parameters, the suggested value calculation unit 21 may start the calculation of the suggested parameter value with this timing as a trigger. In this case, the suggested value calculation unit 21 calculates the parameter value of each of a plurality of parameters while reflecting the change.

The suggested value output unit 31 outputs the suggested parameter value calculated by the suggested value calculation unit 21. Specific means which is used when the suggested value output unit 31 outputs the suggested parameter value is not particularly limited, and may be realized by applying all sorts of output devices. When the user interface shown in FIG. 2 is used, suggested value output unit 31 outputs the suggested parameter value to the column "recommended value" associated with each of a plurality of parameters (vegetable intake amount, extra work time, sleeping time, smoking amount).

According to the simulation system 1 having the expected value reception unit 11, the condition holding unit 40, the condition reception unit 12, the suggested value calculation unit 21, and the suggested value output unit 31, in a simulation which calculates the values of a plurality of parameters such that the expected value is obtained as the simulation value, the user can set a condition to be satisfied as the value of each parameter by the designation of information (degree-of-variation understanding information) for intuitive understanding of the degree of allowable variation, instead of determining and inputting the condition as a numerical range. For this reason, the user can easily set a desired condition to each parameter.

Figure 3:
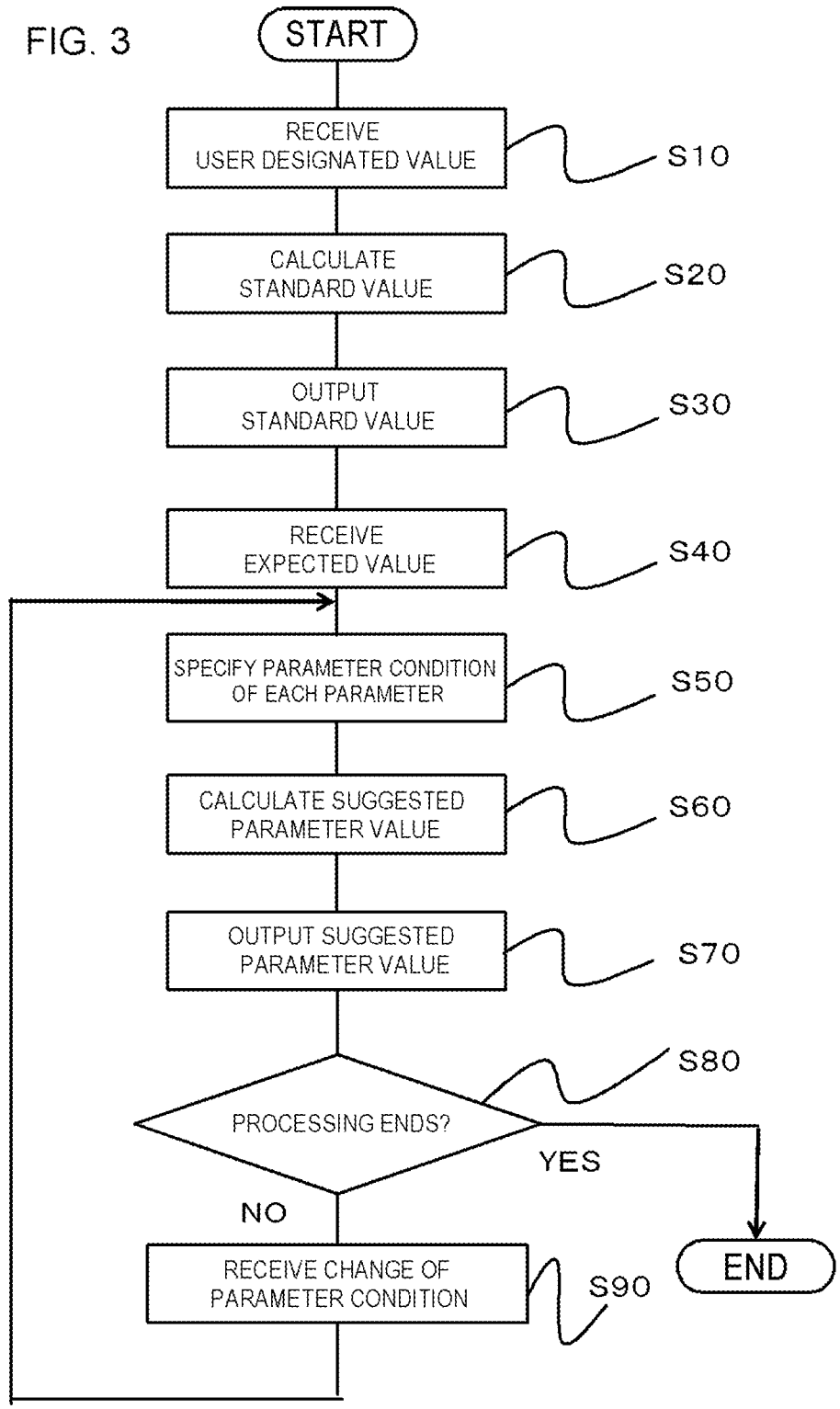
FIG. 3 is a flowchart showing an example of a processing procedure of the simulation system of this embodiment.

Next, an example of a processing procedure of the simulation system 1 of this embodiment will be described. FIG. 3 is a flowchart showing an example of a processing procedure of the simulation system 1 of this embodiment. The processing procedure described below is just an example, and the processing procedure of the simulation system 1 is not limited thereto. Hereinafter, description will be provided also with reference to FIGS. 1 and 2.

First, the parameter input reception unit 13 receives the input of the user designated value (S10). The parameter input reception unit 13 receives, as the user designated value, a value representing the present state of the user of each parameter from the pull-down menu in the column "present value" associated with each of a plurality of parameters (vegetable intake amount, extra work time, sleeping time, smoking amount) of the user interface shown in FIG. 2.

Next, the standard value calculation unit 22 calculates the simulation value (standard value) from the user designated values received in S10 through the first simulation (S20). Next, the standard value output unit 32 outputs the standard value calculated in S20 (S30). In this embodiment, the standard value output from the standard value output unit 32 is displayed in the column "predictive life span" of the user interface shown in FIG. 2.

Next, the expected value reception unit 11 receives an input of the expected value (S40). The expected value reception unit 11 receives the target life span as the expected value from the pull-down menu in the column "target life span" of the user interface shown in FIG. 2. At this time, the user can determine a desired expected value with reference to the user designated values (the column "present value") input in S10 and the standard value (the column "predictive life span") output in S30.

Next, for example, the suggested value calculation unit 21 specifies the parameter condition set to each parameter (S50). The processing in which the suggested value calculation unit 21 realizes the specification may be the following processing.

First, the condition reception unit 12 receives the setting of the parameter condition from the pull-down menu in the column "will to improve" associated with each of a plurality of parameters (vegetable intake amount, extra work time, sleeping time, smoking amount) of the user interface shown in FIG. 2. The condition holding unit 40 holds a table in which each parameter is associated with the parameter condition set to each parameter, and dynamically changes the content of the table in accordance with the content received by the condition reception unit 12. The suggested value calculation unit 21 specifies the parameter condition set to each parameter with reference to the table.

The timing at which the suggested value calculation unit 21 specifies the parameter condition set to each parameter with reference to the table or the like is not particularly limited, and for example, the timing at which the input of the expected value is received in S40 may be used as a trigger or the timing at which the parameter conditions are set to all of the parameters may be used as a trigger.

Next, the variation range calculation unit 23 calculates the variation range of each of a plurality of parameters on the basis of the parameter condition designated to each parameter. The suggested value calculation unit 21 calculates a combination of the values (suggested parameter values) of a plurality of parameters such that the result of the first simulation becomes the expected value received in S40 so as to fill the calculated variation range (S60). Next, the suggested value output unit 31 outputs the suggested parameter values calculated in S60 (S70). In this embodiment, the suggested parameter value output from the suggested value output unit 31 are displayed in the column "recommended value" associated with a plurality of parameters (vegetable intake amount, extra work time, sleeping time, smoking amount) of the user interface shown in FIG. 2.

Next, if an input to end the processing is received in S80 (Yes), the simulation system 1 ends the processing.

When the input to end the processing is not received in S80 (No), the simulation system 1 waits for receiving an input to change the parameter condition of one or more parameters.

If the input to change the parameter condition of one or more parameters is received (S90), the condition reception unit 12 returns to S50, and repeats the same processing as described above.

That is, when the condition reception unit 12 receives the input to change the parameter condition of one or more parameters (S90), for example, "the table in which the parameter condition set to each parameter is associated with each parameter" held in the condition holding unit 40 is updated in accordance with the content received by the condition reception unit 12. For example, the suggested value calculation unit 21 specifies the parameter condition set to each of a plurality of parameters at this time with reference to the table after the update (for each parameter with the change of the parameter condition received, the parameter condition after the change) (S50). The simulation system 1 repeats the processing after S60.

When the condition reception unit 12 receives an input to change the parameter condition of one or more parameters in the column "will to improve" associated with each of a plurality of parameters (vegetable intake amount, extra work time, sleeping time, and smoking amount) in the user interface shown in FIG. 2, the display of the column is changed. Accordingly, the values in the column "recommended value" are changed. The "change in the column of the recommended value" is realized by causing the suggested value calculation unit 21 to recalculate the suggested parameter values while reflecting the change of the parameter condition and causing the suggested value output unit 31 to output the suggested parameter values.

According to the simulation system 1 of this embodiment, it becomes possible for the user to explicitly and efficiently input the parameter condition to each parameter, or to dynamically designate and change the parameter condition during the execution of the simulation.

<Second Embodiment>

In this embodiment, a simulation system 1 having a user interface different from the first embodiment will be described. In this embodiment, as in the first embodiment, an example where the first simulation is a life span prediction simulation will be described.

Figure 20:
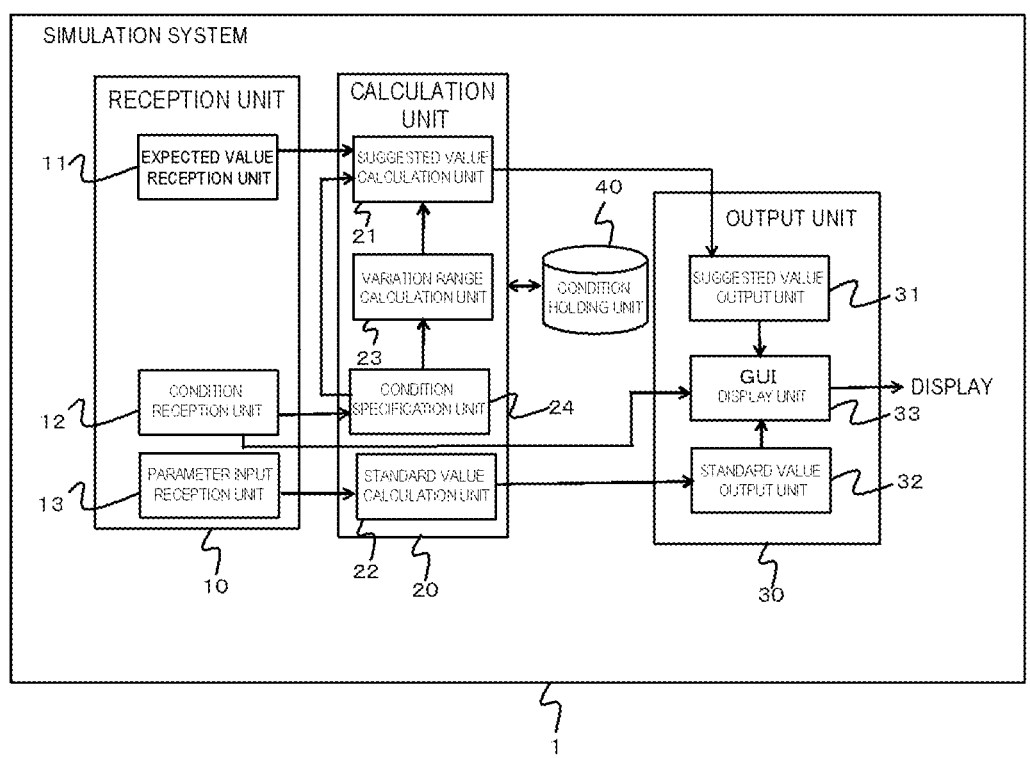
FIG. 20 is an example of a functional block diagram of the simulation system of this embodiment.

FIG. 20 is a functional block diagram showing an example of the configuration of the simulation system 1 of this embodiment. As shown in FIG. 20, the simulation system 1 of this embodiment has a configuration different from the first embodiment in that a GUI display unit 33 and a condition specification unit 24 are further provided.

Hereinafter, the configuration of the GUI display unit 33 and the condition specification unit 24 will be described. In regard to other parts, only a difference from the first embodiment will be described.

The GUI display unit 33 displays a plurality of parameter components corresponding to a plurality of parameters on the display. The GUI display unit 33 displays a plurality of parameter condition components corresponding to a plurality of parameter conditions set to a plurality of parameters on the display.

Figure 4:
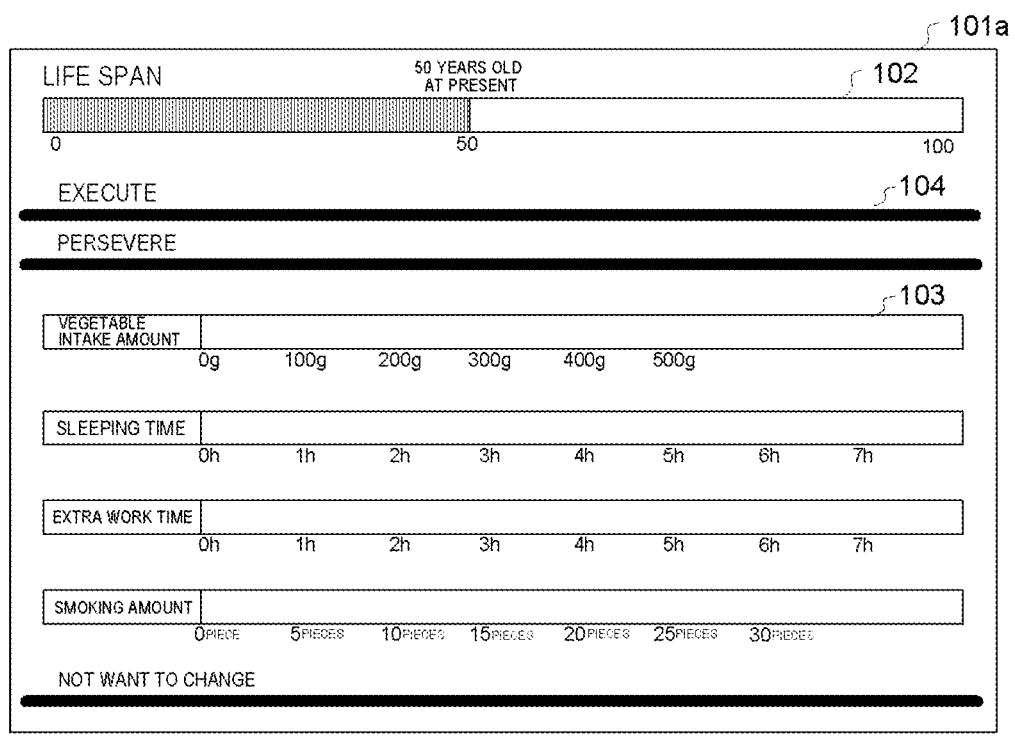
FIG. 4 is a diagram showing an example of a user interface of the simulation system of this embodiment.

FIG. 4 shows an example of a user interface of this embodiment.

In a user interface 101*a* shown in FIG. 4, the GUI display unit 33 displays four parameter components 103 corresponding to four parameters of "vegetable intake amount", "sleeping time", "extra work time", and "smoking amount". Each parameter component 103 has a linear graph, and the value of each parameter can be displayed on the graph.

In the user interface 101*a* shown in FIG. 4, the GUI display unit 33 displays three parameter condition components 104 corresponding to three parameter conditions. Three kinds of degree-of-variation understanding information of "execute", "persevere", and "not want to change" are assigned to the parameter condition components 104.

FIG. 17 shows an example of a part of the internal configuration of the condition holding unit 40 of this embodiment.

The computer condition associated with the degree-of-variation understanding information "persevere" may be, for example, "the value (X) of the parameter may change from the predetermined value (Y) in the direction of extension of the life span if possible ($Y \leq X \leq A$ or $B \leq X \leq Y$)". The predetermined value (Y) may be a value set in advance, such as the average value of a Japanese person, or may be a user designated value.

The computer condition associated with the degree-of-variation understanding information "not want to change" may be, for example, "the value (X) of the parameter does not change from the predetermined value (Y) ($X=Y$)".

The computer condition associated with the degree-of-variation understanding information "execute" may be, for example, "the value (X) of the parameter does not change from the suggested parameter value (Z) when "execute" is set ($X=Z$)". The suggested parameter value (Z) may be, for example, a value displayed in the parameter component 103 shown in FIG. 4 at that time.

As described in the first embodiment, if the number of parameter conditions is limited, the number of parameters which are assigned to each condition can increase and can be processed in groups, and it can be expected that the processing efficiency of the simulation system 1 is improved.

Returning to FIG. 4, a simulation value component 102 for displaying the simulation value of the life span prediction simulation is displayed in the user interface 101*a*. The simulation value component 102 has a linear graph, and the simulation value can be displayed on the graph. As shown in FIG. 4, the present age (present value) of the user received from the user may be displayed in the simulation value component 102.

The linear graph of the parameter component 103 and the linear graph of the simulation value component 102 are arranged in parallel in the user interface 101*a*.

Returning to FIG. 20, the condition specification unit 24 assigns one parameter condition component 104 to the first parameter component 103 by means of the display position of the first parameter component 103 and the display position of each of a plurality of parameter condition components 104. The condition specification unit 24 specifies the parameter condition assigned to the parameter condition component as the parameter condition set to the parameter corresponding to the first parameter component 103.

Specifically, first, the condition specification unit 24 specifies the display position of each of a plurality of parameter components 103 on the display screen and the display position of each of a plurality of parameter condition components 104 on the display screen. For example, the simulation system 1 holds a table (hereinafter, referred to as "display position table") in which the display position is associated with each of a plurality of parameter components 103 and a plurality of parameter condition components 104. The condition specification unit 24 specifies the display position of each component with reference to the display position table.

The display position of each component may be expressed as the coordinate point of a predetermined place (for example: the center point of each component) by means of the coordinate axes set on the display screen on which a plurality of parameter components 103 and a plurality of parameter condition components 104 are displayed.

Next, the condition specification unit 24 assigns one parameter condition component 104 to each of a plurality of parameter components 103 by means of the display position of each component in accordance with a rule (hereinafter, referred to as "assigning rule").

The assigning rule is not particularly limited insofar as one parameter condition component can be assigned to one parameter component. For example, the assigning rule defines a predetermined separate region for each parameter condition component 104 by means of the display position of each of a plurality of parameter condition components 104. A rule which defines "one parameter condition component 104 is assigned to each parameter component 1 on the basis of a region where each parameter component is positioned" may be used. Besides, the assigning rule may be a rule which defines "the closest parameter condition component 104 positioned above the first parameter component 103 is assigned to the first parameter component 103". These are just an example, and other assigning rules may be used.

Next, the condition specification unit 24 specifies the parameter condition corresponding to the parameter condition component 104 assigned to the first parameter component 103 as the parameter condition set to the parameter corresponding to the first parameter component 103.

For example, the simulation system 1 holds a table (first table) in which each of a plurality of parameter components 103 and each of a plurality of parameters are assigned to each other. The simulation system 1 holds a table (second table) in which each of a plurality of parameter condition components 104 and each of a plurality of parameter conditions are assigned to each other.

The condition specification unit 24 specifies the parameter condition corresponding to the parameter condition component 104 assigned to the first parameter component 103 as the parameter condition set to the parameter corresponding to the first parameter component 103 by means of the display position table, the assigning rule, the first table, and the second table.

In FIG. 4, if the assigning rule is configured such that the closest parameter condition component 104 positioned above the first parameter component 103 is assigned to the "first parameter component 103", the condition specification unit 24 specifies the parameter condition "persevere" for all of the parameters.

The condition reception unit 12 of this embodiment receives the input to change the display position of each of a plurality of parameter components 103 displayed on the GUI display unit 33 and/or the input to change the display position of each of a plurality of parameter condition components 104, thereby receiving the input to set any parameter condition to each of a plurality of parameters. Means which is used when the condition reception unit 12 receives the input to change the display position of each of the parameter components 103 and/or the input to change the display position of each of a plurality of parameter condition components 104 is not particularly limited, and may be realized by applying all sorts of input devices. The condition reception unit 12 may receive an operation to the parameter component 103 and/or the parameter condition component 104 in the user interface 101a, thereby receiving the input to change the display position of each component. If the condition reception unit 12 receives the input, the display position table is updated.

Figure 5:
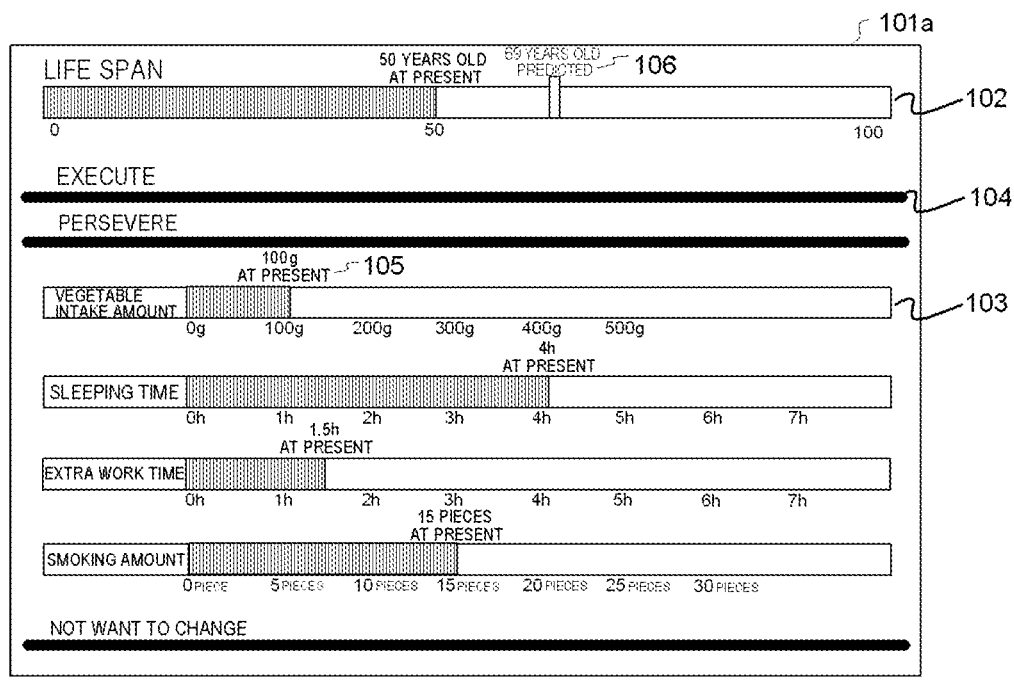
FIG. 5 is a diagram showing an example of a user interface of the simulation system of this embodiment.

If the parameter input reception unit 13 receives an input of user designated values (for example: present values) in the user interface 101a (FIG. 4), as shown in FIG. 5, the user designated values 105 are displayed in the parameter components 103. A standard value 106 calculated by the standard value calculation unit 22 on the basis of the user designated values 105 is displayed in the simulation value component 102 by the standard value output unit 32. The parameter input reception unit 13 may receive an operation to each of the parameter components 103 in the user interface 101a, thereby receiving the input of the user designated values.

Figure 6:
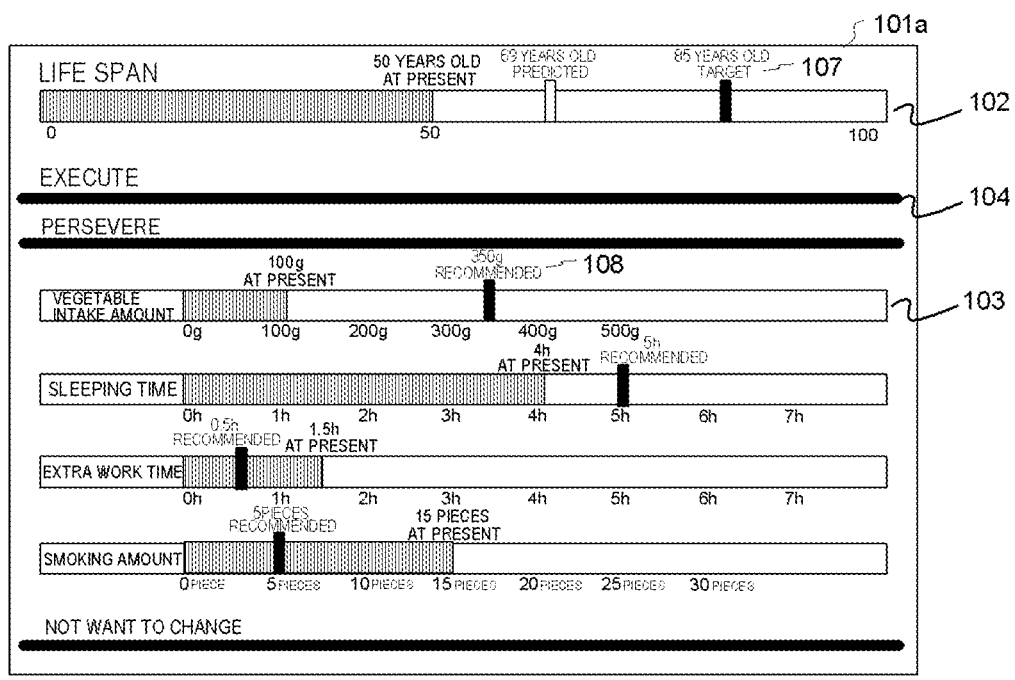
FIG. 6 is a diagram showing an example of a user interface of the simulation system of this embodiment.

If the expected value reception unit 11 receives an input of an expected value in the user interface 101a, as shown in FIG. 6, the expected value 107 is displayed in the simulation value component 102. Suggested parameter values 108 (in the drawing, recommended values) calculated by the suggested value calculation unit 21 on the basis of the parameter conditions set to the parameters and the expected value 107 are displayed in the parameter components 103 by the suggested value output unit 31. The expected value reception unit 11 may receive an operation to the simulation value component 102 in the user interface 101a, thereby receiving the input of the expected value.

Figure 7:
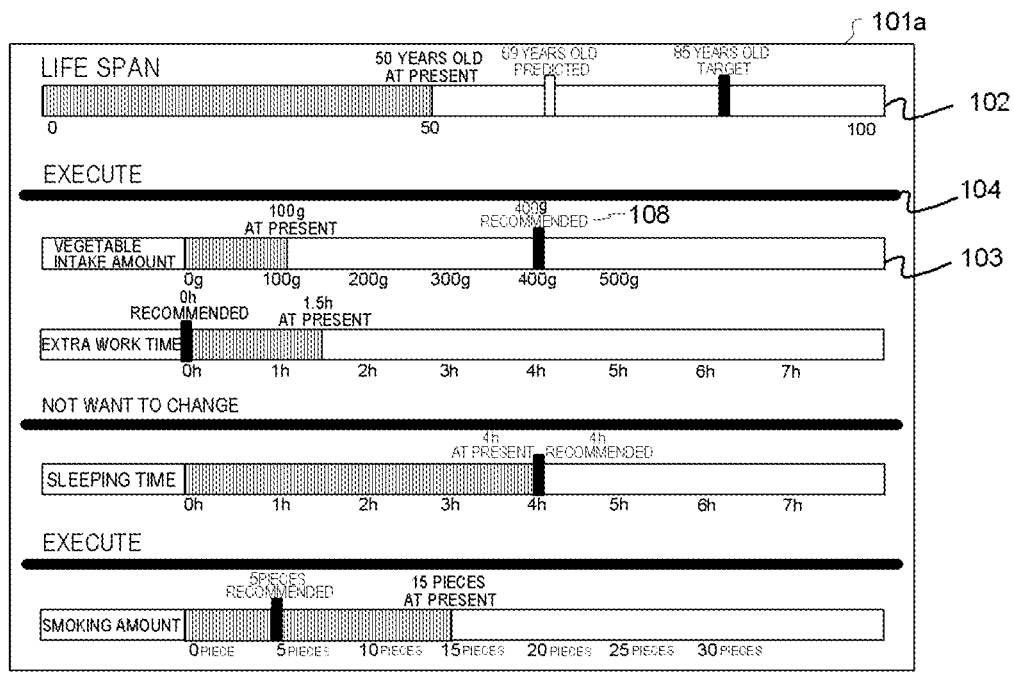
FIG. 7 is a diagram showing an example of a user interface of the simulation system of this embodiment.

When the condition reception unit 12 receives an input to change the display positions of the parameter components 103 and/or the parameter condition components 104 in the user interface 101a in the state shown in FIG. 6, the display positions are changed as shown in FIG. 7. When this happens, the display position table is rewritten with the changes in the display positions. The condition specification unit 24 specifies the parameter condition set to each of a plurality of parameters on the basis of the display position of each of a plurality of parameter components 103 and the display position of each of a plurality of parameter condition components 104 after the changes in the display positions.

In FIG. 7, if the assigning rule is that "the closest parameter condition component 104 positioned above the first parameter component 103 is assigned to the first parameter component 103", the condition specification unit 24 specifies the parameter condition "persevere" to the parameters "vegetable intake amount" and "extra work time", specifies the parameter condition "not want to change" to the parameter "sleeping time", and specifies the parameter condition "execute" to the parameter "smoking amount".

Thereafter, the suggested parameter values are recalculated while reflecting the changes in the parameter conditions (suggested value calculation unit 23), and the recalculated suggested parameter values 108 (in the drawing, recommended values) are displayed in the parameter components 103 (suggested value output unit 31).

The user interface of the simulation system 1 of this embodiment may have other modifications.

For example, as means for receiving an input from the user, a text box, a radio button, a check box, a list box, a drop-down list, or the like may be used. Means for receiving an input from a spin button, a slider, a directly operable graph, or the like may be used. The directly operable graph corresponds to, for example, a graph in which a value represented by the graph, the graph itself, or a knob or button arranged on the graph, can be operated by a click or a drag-and-drop of a pointing device, such as a mouse, a tablet, a trackball, or a joystick. A physical button, lever, knob, slider, dial, or the like may be used.

The above is for illustration, and the invention is not limited thereto. For example, when the means for receiving an input from the user is expressed using a directly operable graph, an input of a value to be simulated may be received by a click of a pointing device at a point on a directly operable bar graph. For example, when the means for receiving an input from the user is expressed using a directly operable bar graph, a value to be simulated may be input by a click of a pointing device to a button arranged on the directly operable bar graph. For example, when the means for receiving an input from the user is expressed using a directly operable graph, the movement of the parameter may be input by dragging a knob on the directly operable graph using a pointing device. The above is for illustration, and the acquisition of the input of the simulation is not limited to the above description.

Various kinds of data (expected value, suggested parameter value, standard value, suggested parameter value, user designated value, and the like) may be displayed using all sorts of means, such as text, table, and graph. However, the invention is not limited thereto.

That is, when various kinds of data are displayed in text, these may be expressed with numerical values. When various kinds of data are expressed with graphs, data may be expressed with all sorts of graphs including a bar graph, a circular graph, a band graph, a polygonal line graph, and a radar chart. When various kinds of data are expressed with graphs, and an input of data is received on a directly operable graph, data may be expressed simultaneously on a directly operable graph on which an input of a simulation is acquired. When an input of a simulation is acquired with a directly operable bar graph, a simulation result may be expressed on a directly operable bar graph on which the input of the simulation is acquired.

The parameter condition component 104 may be dotted or curved. The shape of the parameter condition component 104 may be a shape, a circle, a polygonal, or an ellipse, which delimits a region. In this case, the condition specification unit 24 may assign one parameter condition component 104 to each of a plurality of parameter components 103 by means of the region delimited by the parameter condition component 104.

According to the simulation system 1 of this embodiment having this user interface, the user can easily and intuitively set and change a desired condition. That is, a highly user-friendly system is realized. The same functional effects as the first embodiment can be realized.

<Third Embodiment>

In this embodiment, an example where the first simulation is a housing loan repayment period simulation will be described. The configuration of a simulation system 1 of this embodiment may have the same configuration as the simulation system 1 of the first embodiment or the simulation system 1 of the second embodiment.

Figure 8:
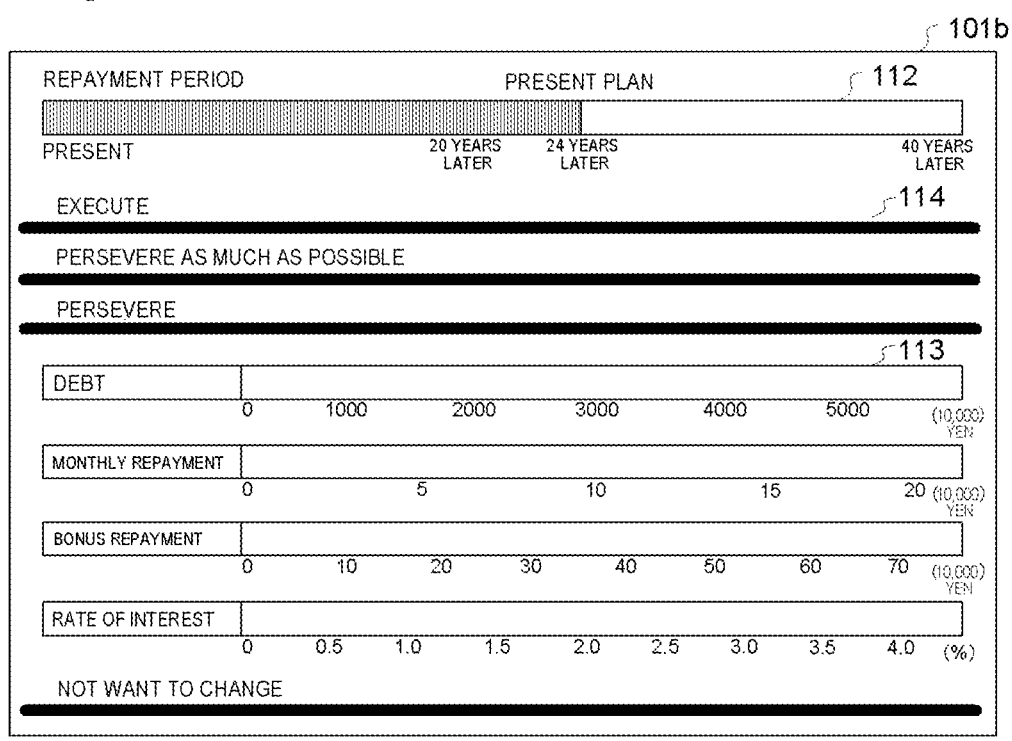
FIG. 8 is a diagram showing an example of a user interface of the simulation system of this embodiment.

FIG. 8 is a diagram showing an example of a user interface of the simulation system 1 of this embodiment. The basic configuration of a user interface 101b shown in FIG. 8 is the same as the configuration of the user interface 101a shown in FIG. 4 described in the second embodiment, thus detailed description will not be repeated.

In the user interface 101b shown in FIG. 8, a simulation value (repayment period) of a housing loan repayment period simulation is displayed in a simulation value component 112 for displaying a simulation value. As shown in FIG. 8, a present repayment plan (repayment period) input from the user may be displayed in the simulation value component 112.

In the user interface 101b shown in FIG. 8, four parameter components 113 corresponding to four parameters of "debt", "monthly repayment", "bonus repayment", and "rate of interest" are displayed.

Four parameter condition components 114 corresponding to four parameter conditions are displayed in the user interface 101b shown in FIG. 8. Four kinds of degree-of-variation understanding information of "execute", "persevere if possible", "persevere", and "not want to change" are assigned to the parameter condition components 114.

FIG. 18 shows an example of a part of the internal configuration of a condition holding unit 40 of this embodiment.

The computer condition which is associated with the degree-of-variation understanding information "persevere if possible" may be, for example, "the value (X) of the parameter may change from a user designated value to the change rate of 50% in the decreasing direction of the repayment period (W≤X≤1.5W≤A or B≤0.5W≤X≤W)".

The computer condition which is associated with the degree-of-variation understanding information "persevere" may be, for example, "the value (X) of the parameter may change from the user designated value (W) to the change rate of 25% in the decreasing direction of the repayment period (W≤X≤1.25W≤A or B≤0.75W≤X≤W)".

The computer condition which is associated with the degree-of-variation understanding information "not want to change" may be, for example, "the value (X) of the parameter does not change from the user designated value (W) (X=W)".

The computer condition which is associated with the degree-of-variation understanding information "execute" may be, for example, "the value (X) of the parameter does not change from the suggested parameter value (Z) when "execute" is set (X=Z)".

According to the simulation system 1 of this embodiment, the same functional effects as in the first embodiment and the second embodiment can be realized.

<Fourth Embodiment>

In this embodiment, an example where the first simulation is a product ordering simulation will be described. The configuration of a simulation system 1 of this embodiment may be the same as the configuration of the simulation system 1 of the first embodiment or the configuration of the simulation system 1 of the second embodiment.

Figure 9:
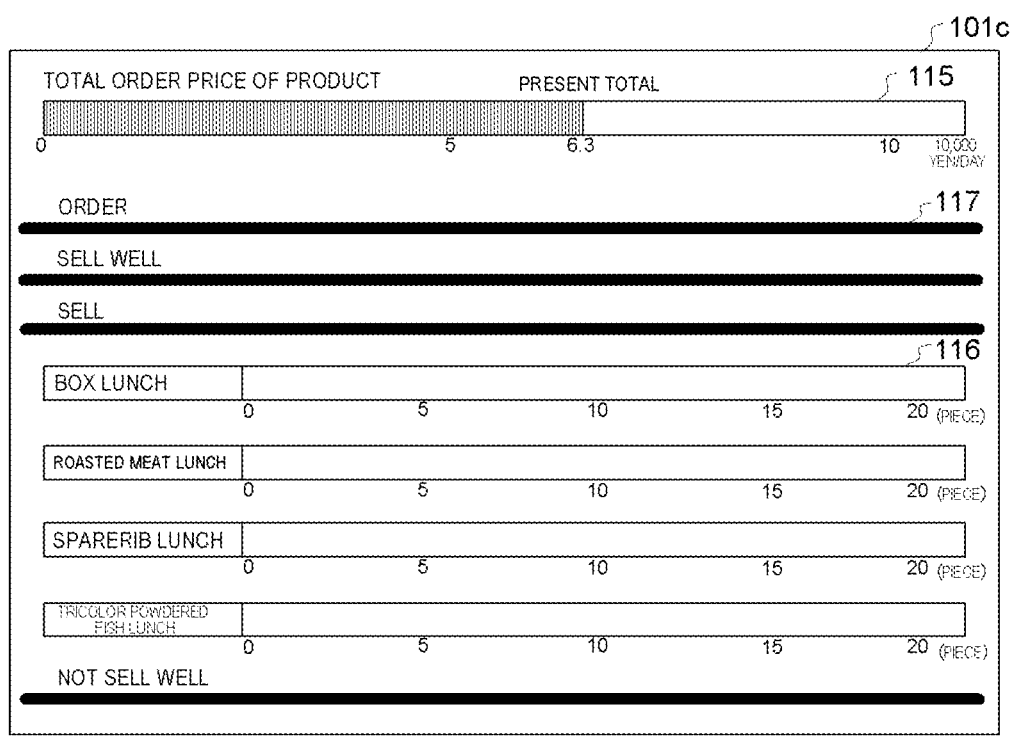
FIG. 9 is a diagram showing an example of a user interface of the simulation system of this embodiment.

Just for reference, an example of a user interface of the simulation system 1 of this embodiment is shown in FIG. 9. The basic configuration of a user interface 101c shown in FIG. 9 is the same as the configuration of the user interface 101a shown in FIG. 4 described in the second embodiment, thus detailed description will not be repeated.

In the user interface 101c shown in FIG. 9, a simulation result (total order price of product) of a product ordering simulation is displayed in a simulation value component 115 for displaying a simulation value. As shown in FIG. 9, a present value (total) input from the user may be displayed in the simulation value component 115.

In the user interface 101c shown in FIG. 9, four parameter components 116 corresponding to four parameters of "box lunch", "roasted box lunch", "sparerib lunch", and "tricolor powdered fish lunch" are displayed.

In the user interface 101c shown in FIG. 9, three parameter condition components 104 corresponding to three parameter conditions are displayed. Three kinds of degree-of-variation understanding information of "execute", "persevere", and "not want to change" are assigned to the parameter condition components 114.

FIG. 19 shows an example of a part of the internal configuration of a condition holding unit 40 of this embodiment.

The computer condition which is associated with the degree-of-variation understanding information "not sell well" may be, for example, "the value (X) of the parameter is in a predetermined range (for example: equal to or greater than 1 and equal to or smaller than 5) (1×5)".

The computer condition which is associated with the degree-of-variation understanding information "sell" may be, for example, "the value (X) of the parameter is set to be greater than the value (X') of the parameter to which the parameter condition "not sell well" is set (X'≤X)".

The computer condition which is associated with the degree-of-variation understanding information "sell well" may be, for example, "the value (X) of the parameter is set to a value greater than the value (X") of the parameter to which the parameter condition "sell" is set (X"≤X)".

The computer condition which is associated with the degree-of-variation understanding information "order" may be, for example, "the value (X) of the parameter does not change from the suggested parameter value (Z) when "order" is set (X=Z)".

According to the simulation system 1 of this embodiment, the same functional effects as in the first embodiment to the third embodiment can be realized.

<Fifth Embodiment>

A simulation system 1 of this embodiment is configured by changing a part of the configuration of the user interface of one of the second embodiment to the fourth embodiment.

Figure 10:
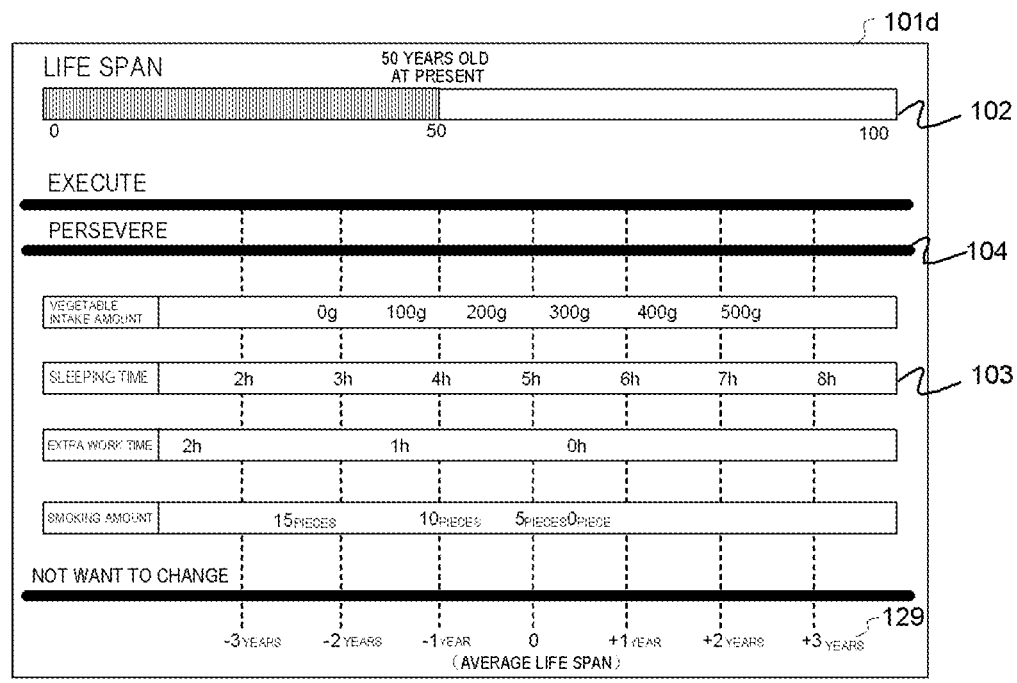
FIG. 10 is a diagram showing an example of a user interface of the simulation system of this embodiment.

FIG. 10 shows an example of a user interface of the simulation system 1 of this embodiment. A user interface 101d shown in FIG. 10 is different from the user interface shown in FIG. 4 in that a configuration in which the user can more intuitively understand the degree of influence of change in the value of each parameter on the result (simulation value) of the first simulation is made. Other parts are the same as those in the user interface shown in FIG. 4.

The degree of influence refers to "in which of the plus direction and the minus direction the simulation value changes when the value of each parameter changes in the plus direction or the minus direction", "how much the simulation value changes when the value of each parameter changes by a predetermined value", or the like. The above is for illustration, and the degree of influence is not limited thereto.

In the user interface 101d shown in FIG. 10, the value of the parameter and the simulation value are displayed with the same means (linear graph), and are substantially arranged in parallel, thereby allowing intuitive understanding of the degree of influence. The configuration is the same as the user interface 101a shown in FIG. 4.

In the user interface 101d shown in FIG. 10, the direction in which the value of the parameter changes on the linear graph of the parameter component 103 coincides with the direction in which the simulation value changes on the linear graph of the simulation value component 102 due to the change. Specifically, in FIG. 10, the simulation value (predictive life span) is displayed to increase in the right direction of the drawing. Since the parameter "vegetable intake amount" has the relationship that the simulation value (predictive life span) increases as the vegetable intake amount increases, the value is displayed to increase in the right direction of the drawing. Since the parameter "smoking amount" has the relationship that the simulation value (predictive life span) increases as the smoking amount is lowered, the value is displayed to be lowered in the right direction of the drawing. With this display, the user can intuitively understand the degree of influence of change in the value of each parameter on the simulation value.

In the user interface 101*d* shown in FIG. 10, a scale 129 which represents the degree of influence of change (amount of change) in each of the values of a plurality of parameters on change (amount of change) in the simulation value is displayed. The scale of each of the parameter components 103 is adjusted such that the amount of change in the value of each parameter coincides with the amount of change in the simulation value (predictive life span value) with the amount of change.

Specifically, in the example shown in FIG. 10, the relationship between the parameter "vegetable intake amount" and the simulation value "predictive life span" is that the life span becomes shorter by two years than average when the vegetable intake amount is 0 g, reaches the average life span when the vegetable intake amount is 250 g, and becomes longer by two years than average when the vegetable intake amount is 500 g.

The relationship between the parameter "sleeping time" and the simulation value "predictive life span" is that the life span becomes shorter by three years than average when the sleeping time is 2 h, becomes shorter by two years than average when the sleeping time is 3 h, becomes shorter by one year when the sleeping time is 4 h, reaches the average life span when the sleeping time is 5 h, becomes longer by one year than average when the sleeping time is 6 h, becomes longer by two years than average when the sleeping time is 6 h, and becomes longer by three years than average when the sleeping time is 7 h.

While the degree of influence of each of the parameters "vegetable intake amount" and "sleeping time" on the simulation value "predictive life span" monotonically increases linearly, change in the value of "predictive life span" due to "sleeping time" is larger than due to "vegetable intake amount", and the degree of influence differs.

The relationship between the parameter "extra work time" and the simulation value "predictive life span" is that the life span becomes longer by 0.5 years than average when the extra work time is 0 h, becomes shorter by 1.5 years than average when the extra work time is 1 h, and becomes shorter by 3.5 years than average when the extra work time is 2 h.

Although the degree of influence of each of the parameters "extra work time" and "sleeping time" on the simulation value "predictive life span" has a linear shape, "extra work time" monotonically decreases in the increasing direction of the value of "predictive life span", and "sleeping time" monotonically increases in the corresponding direction, that is, both are inversed.

The relationship between the parameter "smoking amount" and the simulation value "predictive life span" is that the life span becomes longer by 0.5 years than average when the smoking amount is 0 piece, reaches the average life span when the smoking amount is 5 pieces, becomes shorter by one year than average when the smoking amount is 10 pieces, and becomes shorter by 2.5 years than average when the smoking amount is 15 pieces.

Although the degree of influence of each of the parameters "smoking amount" and "extra work time" on "predictive life span" decreases in the increasing direction of the value of "predictive life span", "extra work time" monotonically decreases, and "smoking amount" exponentially decreases, that is, the way of change in the value of "predictive life span" differs.

The user can intuitively understand the feature of the degree of influence from the user interface 101*d* shown in FIG. 10.

The degree of influence represented by the scale 129 may be also expressed by all sorts of means, such as text, table, and graph. For example, when the degree of influence is expressed in text, the directions of change in the value of the parameter and change in the value to be simulated may be expressed by numerical values. When the degree of influence is expressed with a graph, and when an input value of a simulation is received by a directly operable graph, the directions of change in the value of the parameter and change in the simulation value may be expressed simultaneously on a graph which receives the input of the simulation value. For example, when an input value of a simulation is received by a directly operable bar graph, the directions of change in the value of the parameter as the degree of influence and change in the corresponding simulation value may be expressed on a directly operable graph which receives the input of the simulation value.

In this embodiment, since the degree of influence of each parameter on the value to be simulated is displayed, when the user sets the parameter condition, it can be predicted how the simulation value changes. Accordingly, the user can efficiently and effectively set a predetermined condition. As a result, a desired combination of the values of the parameters is searched, thereby shortening an operation time until a desired combination of the values of the parameters is reached and efficiently performing a simulation.

<Sixth Embodiment>

A simulation system 1 of this embodiment has the same basic configuration as the configuration of one of the first embodiment to the fifth embodiment, and is different from the foregoing embodiments in that a variation range setting reception unit is selectively provided for each parameter which receives an input to set the variation range of the value of the parameter.

Means which is used when the variation range setting reception unit receives the input to set the variation range for each parameter is not particularly limited, and may be realized by applying all sorts of input devices.

According to the simulation system 1 of this embodiment, the user sets the variation range with numerical values for the parameters which the user is sufficiently familiar, and can impose desired restrictions with the parameter conditions for other parameters.

Figure 11:
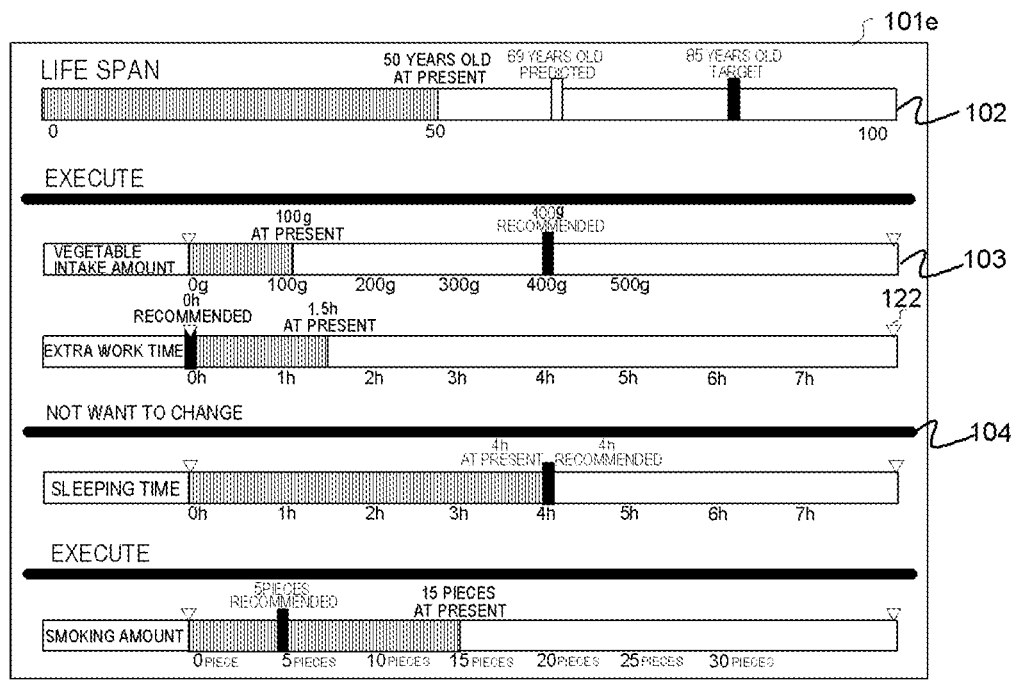
FIG. 11 is a diagram showing an example of a user interface of the simulation system of this embodiment.

An example of a user interface of the simulation system 1 of this embodiment is shown in FIG. 11. FIG. 11 shows a user interface for a life span prediction simulation, and has the same basic configuration as the user interface shown in FIG. 4. Hereinafter, only the configuration of the user interface of this embodiment will be described.

In the case of a user interface 101*e* shown in FIG. 11, two knobs 122 which can set a variation range with numerical values for each parameter are provided in each of the parameter components 103. A region sandwiched between the two knobs 122 becomes a variation range.

Figure 12:
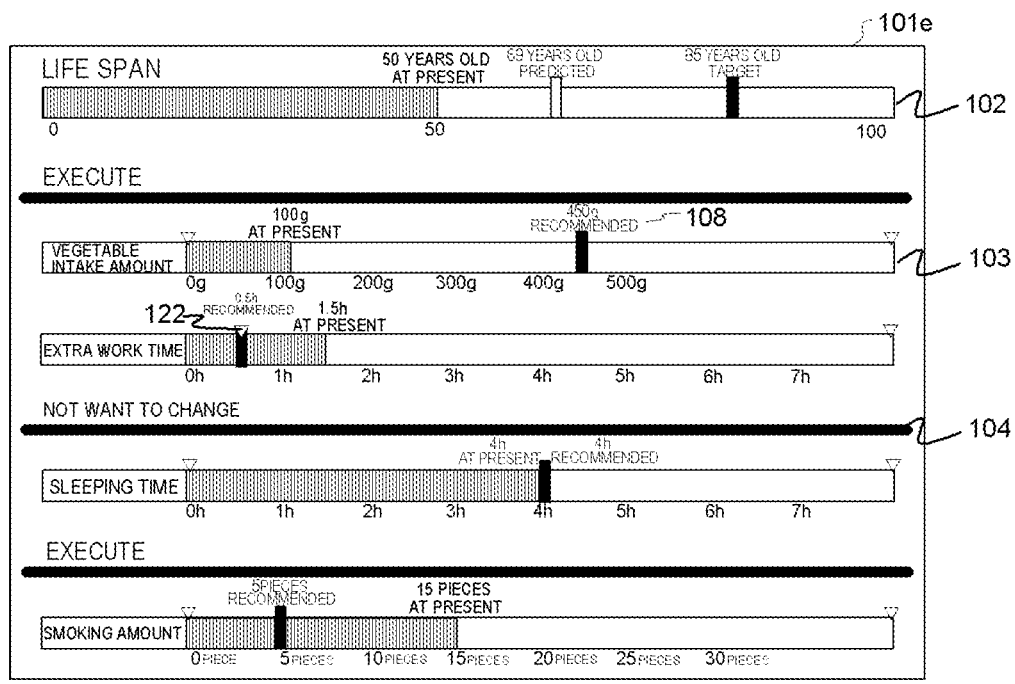
FIG. 12 is a diagram showing an example of a user interface of the simulation system of this embodiment.

When the knob 122 of the parameter component 103 corresponding to the parameter "extra work time" moves in the state shown in FIG. 11, the display position of the knob 122 is, for example, changed as shown in FIG. 12. Accordingly, the user can intuitively understand the set variation range. An input to change the display position of the knob 122 may be realized by receiving an operation to the knob 122 in the user interface 101e.

In a state where the expected value (in FIG. 11, "target" of the simulation value component 102) is designated and at least one of any parameter condition and any variation range is set for all of a plurality of parameters, when the input to change the variation range is received as described above, the suggested value calculation unit 21 may calculate the parameter value of each of a plurality of parameters with this situation as a trigger while reflecting the change in the variation range. The suggested value output unit 31 may output the suggested parameter value calculated by the suggested value calculation unit 21.

As a result, for example, as shown in FIG. 12, suggested parameter values 108 calculated while reflecting the change in the variation range are displayed in the parameter components 103. With comparison of the user interface 101e of FIG. 11 before the display position of the knob 122 changes and the user interface 101e of FIG. 12 after the display position of the knob 122 of the parameter component 103 corresponding to the parameter "extra work time" changes, it is understood that the suggested parameter value 108 (in the drawing, displayed as "recommended") displayed in each parameter component 103 changes.

When the parameter condition and the variation range input with numerical values are set to one parameter, only the variation range input with numerical values may be validated, or both the parameter condition and the variation range input with numerical values may be validated. In the latter case, the variation range obtained by combining the variation range defined on the basis of the parameter condition and the variation range input with numerical values under the and condition or the or condition may be set as the variation range of the value of the parameter.

Figure 13:
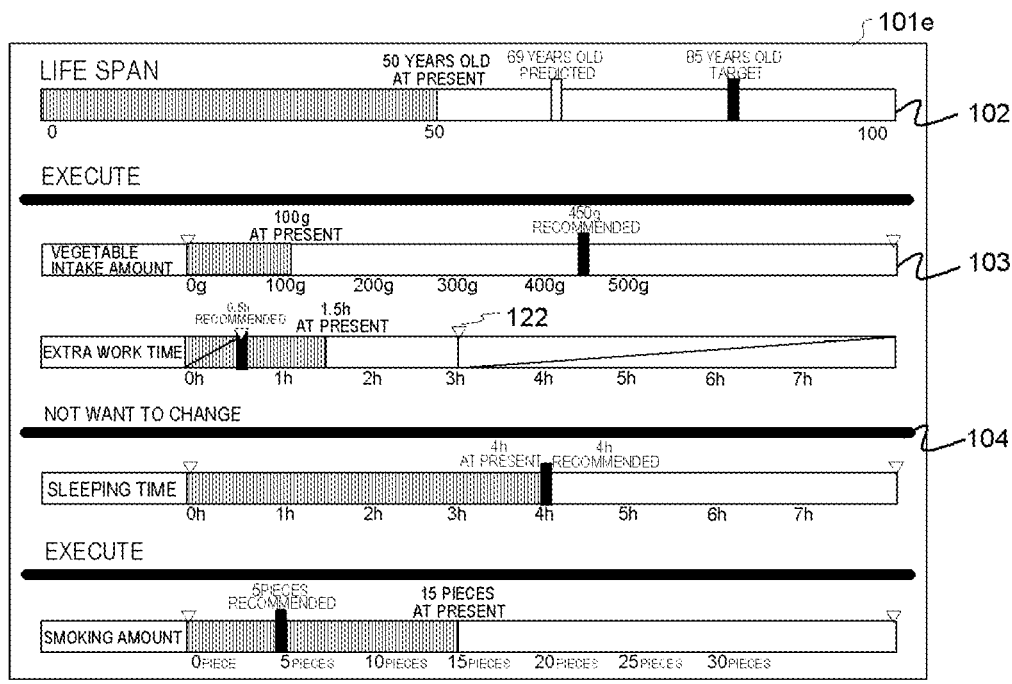
FIG. 13 is a diagram showing an example of a user interface of the simulation system of this embodiment.

In the user interface 101e of this embodiment, as shown in FIG. 13, when the variation range of the value of the parameter is set with numerical values, hatching may be done outside the variation range such that the user can easily understand the set variation range. It should suffice that the user can intuitively understand the variation range, and the means is not limited to the hatching.

Figure 14:
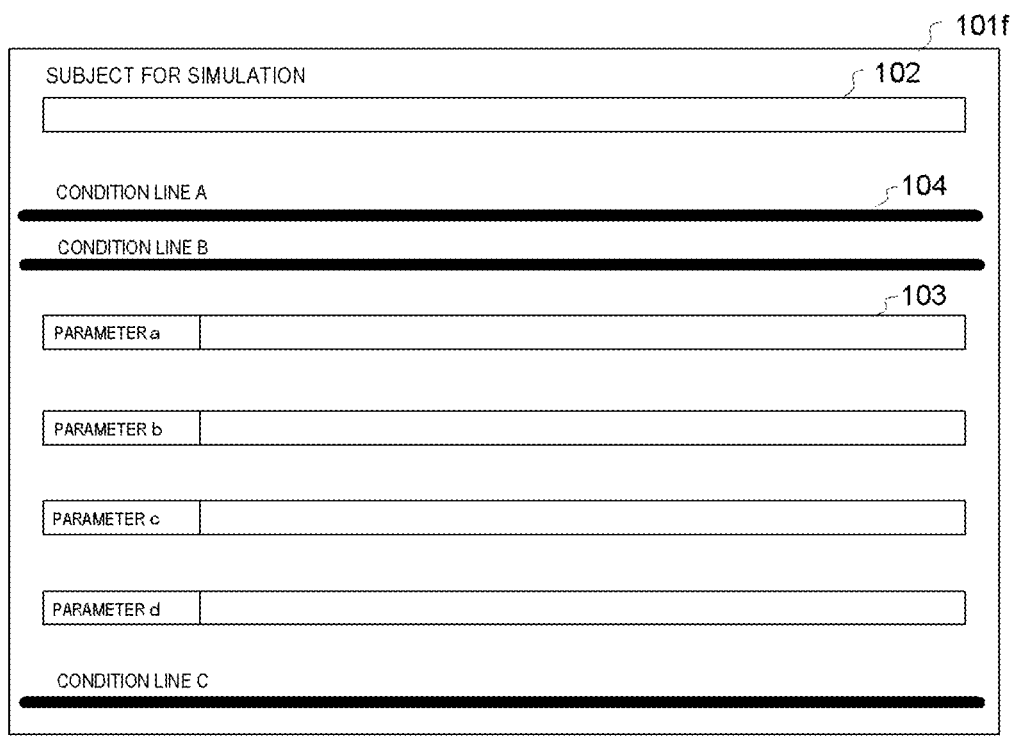
FIG. 14 is a diagram showing an example of a user interface of the simulation system of this embodiment.
Figure 15:
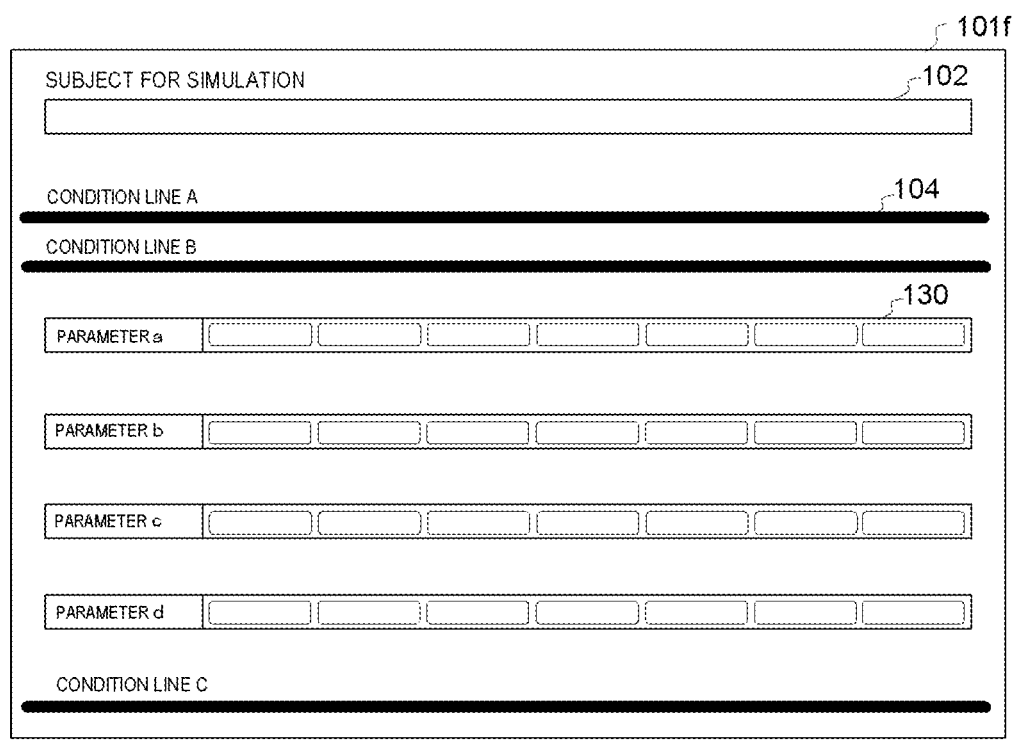
FIG. 15 is a diagram showing an example of a user interface of the simulation system of this embodiment.

The user interface of this embodiment may be one shown in FIGS. 14 and 15. In a user interface 101f shown in FIG. 14, a simulation value component 102 for displaying a simulation value and parameter components 103 for displaying the values of the parameters are displayed on the screen as a directly operable graph, and parameter condition components 104 are displayed on the screen as a directly operable section line. A user interface 101f shown in FIG. 15 shows a case where, when a parameter is a directly operable graph, a method of acquiring an input of a parameter is buttons 130 arranged on the graph.

The embodiments of the invention have been described with reference to the drawings, these embodiments are for illustration of the invention, and various other parts may be used.

For example, in the foregoing embodiments, a case where the display processing system of the invention is a simulation system has been described. However, the display processing system of the invention is not limited to a simulation system. For example, the display processing system of the invention may be a search system which calculates a search result (number of hits, a hit subject, or the like) under a plurality of search conditions. In this case, "search condition" corresponds to "parameter" in the foregoing embodiments, and "search result" corresponds to "simulation value" in the foregoing embodiments. In this way, the display processing system of the invention is effective in a search system which operates on an information processing apparatus having a GUI, or application software having a search function. Specifically, the display processing system of the invention is effective in all sorts of systems, such as web search, paper search, product search, store search, user search, transfer search, and path search, in which a plurality of search conditions are supposed and a predetermined condition is set in each of the search conditions. The above is for illustration, and the invention is not limited thereto. The user interface described in the foregoing embodiments can be applied in all sorts of systems described above.

This application claims priority based on Japanese Patent Application No. 2010-160351, filed Jul. 15, 2010, the disclosure of which is incorporated herein.

The invention claimed is:

1. A display processing system comprising:
   a display;
   a graphical user interface (GUI) display means for displaying a plurality of parameter components corresponding to a plurality of respective parameters and a plurality of parameter condition components, each representing a degree of allowable variation with respect to a present value of each of the plurality of parameters, the parameter condition components corresponding to a plurality of respective conditions set to the plurality of respective parameters on the display;
   condition specification means for determining each degree of allowable variation applied to each of the plurality of parameters based on a relative relationship between the display position of each of the plurality of parameter components and the display position of each of the plurality of parameter condition components; and
   a condition reception unit for receiving an input to change a display position of each of the plurality of parameter components separately and an input to change a display position of each of the plurality of parameter condition components separately.

2. The display processing system according to claim 1, further comprising:
   expected value reception means for receiving designation of an expected value of a simulation value based on the plurality of parameters;
   suggested value calculation means for calculating a suggested value of each of the plurality of parameters by changing the present value of each of the plurality of parameters, based on each degree of allowable variation applied to each of the plurality of parameters determined by the condition specification means, such that the simulation value becomes the expected value; and
   suggested value output means for outputting the suggested values.

3. The display processing system according to claim 2, wherein the GUI display means displays a degree of influence of the change in the present value of each of the plurality of parameters on the change in the simulation value.

4. The display processing system according to claim 1, further comprising:
  standard value calculation means for calculating a standard value being the simulation value based on the present value of each of the plurality of parameters; and
  standard value output means for outputting the standard value.

5. A display processing system comprising:
  a display;
  a graphical user interface (GUI) display means for displaying a plurality of parameter components corresponding to a plurality of respective parameters and a plurality of parameter condition components, each representing a degree of allowable variation with respect to a present value of each of the plurality of parameters, the parameter condition components corresponding to a plurality of respective conditions set to the plurality of respective parameters on the display; and
  condition specification means for determining each degree of allowable variation applied to each of the plurality of parameters based on a relative relationship between the display position of each of the plurality of parameter components and the display position of each of the plurality of parameter condition components,
  wherein the GUI display means displays the plurality of parameter components and the plurality of parameter condition components as bars arranged in parallel with each other in one direction,
  the display processing system further comprises condition reception means for receiving an input to change the order of arrangement of the plurality of parameter components and the plurality of parameter condition components with change in the display positions, and
  the condition specification means determines each degree of allowable variation applied to each of the plurality of parameters based on the order of arrangement.

6. A display processing method comprising:
  a GUI display step of displaying a plurality of parameter components corresponding to a plurality of respective parameters and a plurality of parameter condition components, each representing a degree of allowable variation with respect to a present value of each of the plurality of parameters, the parameter condition components corresponding to a plurality of respective conditions set to the plurality of respective parameters on the display;
  a condition specification step of determining each degree of allowable variation applied to each of the plurality of parameters based on a relative relationship between the display position of each of the plurality of parameter components and the display position of each of the plurality of parameter condition components; and
  a condition reception step of receiving an input to change a display position of each of the plurality of parameter components separately and an input to change a display position of each of the plurality of parameter condition components separately.

7. A non-transitory computer readable recording medium having embodied thereon a program, which when executed by a processor of a display processing system, causes the display processing system to execute a display processing method, the method comprising:
  a GUI display step of displaying a plurality of parameter components corresponding to a plurality of respective parameters and a plurality of parameter condition components, each representing a degree of allowable variation with respect to a present value of each of the plurality of parameters, the parameter condition components corresponding to a plurality of respective conditions set to the plurality of respective parameters on the display;
  a condition specification step of determining each degree of allowable variation applied to each of the plurality of parameters based on a relative relationship between the display position of each of the plurality of parameter components and the display position of each of the plurality of parameter condition components; and
  a condition reception step of receiving an input to change a display position of each of the plurality of parameter components separately and an input to change a display position of each of the plurality of parameter condition components separately.

* * * * *

UNITED STATES PATENT AND TRADEMARK OFFICE
CERTIFICATE OF CORRECTION

PATENT NO. : 9,600,149 B2
APPLICATION NO. : 13/807216
DATED : March 21, 2017
INVENTOR(S) : Junko Togami It is certified that error appears in the above-identified patent and that said Letters Patent is hereby corrected as shown below:

In the Specification

Column 16, Line 20:
"(1x5)" should be replaced by --($1 \leq X \leq 5$)--.

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*